United States Patent [19]

Meistrell

[11] Patent Number: 4,585,003
[45] Date of Patent: Apr. 29, 1986

[54] ICE-PACK RETENTION DEVICE

[75] Inventor: William R. Meistrell, Manhattan Beach, Calif.

[73] Assignee: Dive N' Surf, Inc., Hermosa Beach, Calif.

[21] Appl. No.: 687,909

[22] Filed: Dec. 31, 1984

[51] Int. Cl.⁴ ............................ A61F 7/08; A61F 7/10
[52] U.S. Cl. ...................................... 128/402; 128/403
[58] Field of Search ................... 128/402, 403; 62/530; 383/901

[56] References Cited

U.S. PATENT DOCUMENTS

| | | | |
|---|---|---|---|
| 919,614 | 4/1909 | Meinecke | 128/380 |
| 1,345,906 | 7/1920 | Augustine | 128/402 |
| 3,491,761 | 1/1970 | Baker | 128/403 X |
| 3,889,684 | 6/1975 | Lebold | 128/403 X |
| 4,044,773 | 8/1977 | Baldwin | 128/402 |

Primary Examiner—Anton O. Oechsle
Attorney, Agent, or Firm—William W. Haefliger

[57] ABSTRACT

A heat or cold pack retention device comprises
(a) elongated, insulative, flexible, relatively thin sheet means having two generally parallel, elongated legs joined to a sheet main portion,
(b) said main portion provided with an anchor to anchor the pack, the sheet main portion then engaging and comforming to the shape of the pack,
(c) the legs then being adapted to adjustably wrap about and over the same main portion and hold the pack to a user's body.

4 Claims, 4 Drawing Figures

ICE-PACK RETENTION DEVICE

BACKGROUND OF THE INVENTION

This invention relates generally to cold or hot pack retention devices; and more particularly concerns an improved device which easily attaches to the body of the user, as for example to his knee joint region or elbow joint region, and at the same time allows flexibility of the joint, as during walking, while holding the cold or hot pack in place.

There is a need for means to adequately hold cold or hot packs in place on the bodies of users; and this need is critical as respects user's limbs which are required to flex, in use.

SUMMARY OF THE INVENTION

It is a major object of the invention to provide apparatus meeting the above need, and which also provides additional advantages such as ease of attachment, ease of detachment; blockage of heat transfer from the pack to the exterior (i.e. away from the user's body), and blockage of heat transfer from the exterior to the pack, while it is retained in position; and flexibility and stretchability of the sheet, to best conform to the in-place pack as well as to the user's body to which it is wrapped or retained, in use. Basically, the device comprises:

(a) an elongated, insulative, flexible, relatively thin sheet means having two generally parallel, elongated legs joined to a sheet main portion, (b) said main portion forming a hole to fittingly receive an ice pack neck, the sheet main portion then engaging and conforming to the shape of the ice pack, (c) the legs then being adapted to wrap about and over the sheet main portion and hold the pack to a user's body.

As will appear, the sheet preferably has stretchability, and is in at least partly stretched condition in use, conforming to the shifting shape of the hot or cold pack, and the shifting position of the user's body (such as a limb), allowing the user to walk about with his knee packed, or to flex his packed arm.

It is a further object of the invention to provide an improved device of the above character, wherein the thin sheet comprises an insulative, flexible, stretchable material such as elastomer, a foamed rubber being usable.

It is a further object of the invention to provide an anchor for the pack, as for example a hole in the main portion of the sheet, as will appear.

These and other objects and advantages of the invention, as well as the details of an illustrative embodiment, will be more fully understood from the following specification and drawings, in which:

DRAWING DESCRIPTION

DETAILED DESCRIPTION

Figure 3:
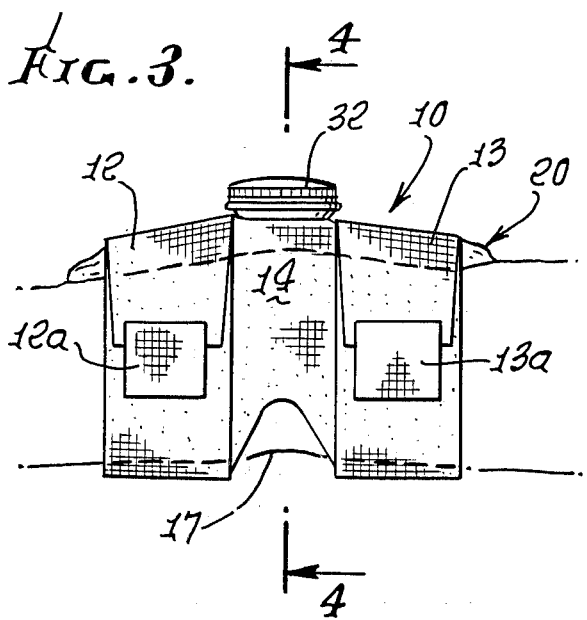
FIG. 3 is a side elevational view showing the sheet wrapped about the knee of a user.
Figure 4:
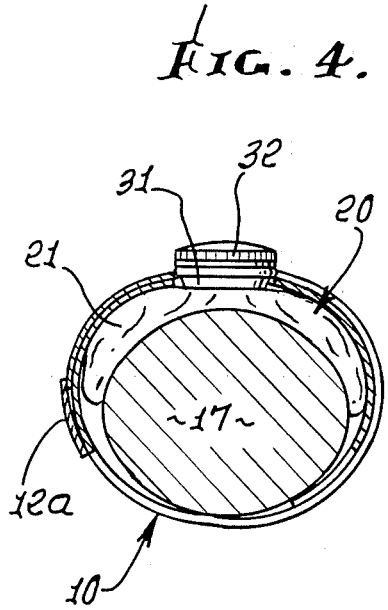
FIG. 4 is a section on lines 4—4 of FIG. 3.

In the drawings, the hot or cold pack retention device 10 comprises an elongated, insulative, flexible, relatively thin sheet 11 having two generally parallel, elongated legs 12 and 13 joined to a sheet main portion 14. The latter may have oppositely extending stub legs 15 and 16, as shown, to be covered by the legs 12 and 13, during wrapping, as in FIGS. 3 and 4. The sheet is preferably stretchable to conform closely to the hot pack 20 positioned over the body extent (such as a knee 17, or elbow joint or neck) for comfortably holding the pack in such position during flexing of the joint, or body, as during walking, or arm flexing. In this regard, the pack 20 may consists of a flexible bag 21 containing cold or warm water, and may contain ice pieces. The bag tubular neck 31 is typically rigid, and mounts a removable cap 32.

Figure 1:
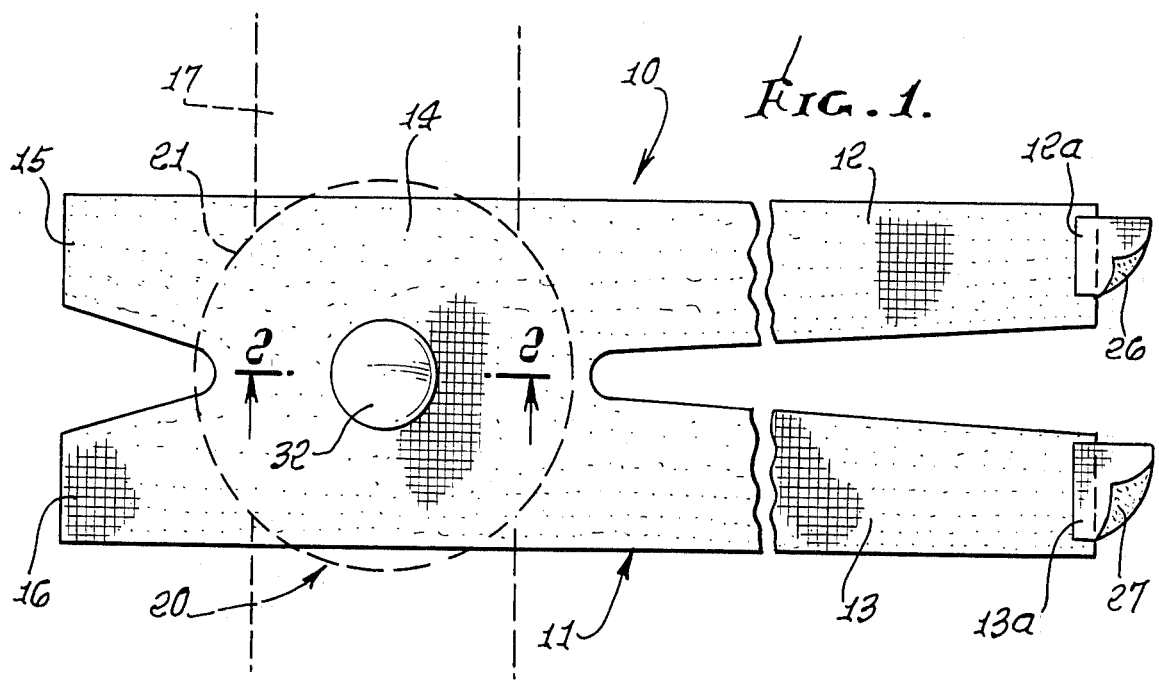
FIG. 1 is a top plan view of a retention device incorporation the invention.
Figure 2:
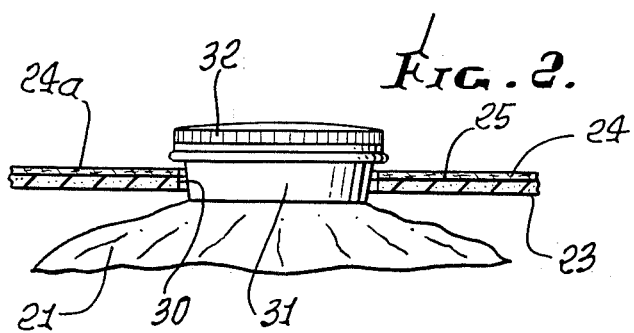
FIG. 2 is a section on lines 2—2 of FIG. 1.

The sheet main portion 14 is provided with an anchor to anchor the pack in position when the sheet main portion is placed over the joint, as is seen in FIG. 1. Note that the sheet main portion is sized to substantially cover and grip the bag, when the latter is partially flattened, as in FIG. 3, with liquid therein. The bag is gripped for example due to the fact that the sheet includes or comprises an underlayer 23 of elastomer, such as foamed rubber (NEOPRENE), of a thickness between about 1/32 inch and ⅛ inch. Such material is stretchable bi-directionally (in all directions) to best conform to the user's flexing joint and to the shifting position of the bag liquid contents, while tensioned, in use.

Attached to the layer 23 (as by adhesive at 25) is an upper or outer layer 24 of fabric having outward facing hook or pile element construction, to attach to pile or hook elements, respectively proximate the ends of the legs, during wrapping. Such elements are indicated at 26 and 27 at the underside of the leg extension 12a and 13a, in FIG. 1, and they removably attach, as by finger pressure to any portion of the outer surface 24a of the layer 24, during wrap-up. Accordingly, the leg extension may be positioned anywhere over the surface 24a of layer 24 on legs 12 or 13, or the main portion 14 of the body, for maximum comfort and adjustably, and in comformance with retention of the bag 21 is curved or other position, over the body joint, or body surface.

The anchor may be generally centrally located on main body portion 14, and may with unusual advantage comprise a through opening or hole 30 through portion 14, sized to loosely, i.e. fittingly receive the tubular neck 31 of the bag 21, slipped through the opening. A cap 32 is shown on the neck, and is removable to change the liquid contents of the bag. Legs 12 and 13 wrap over the pack 20, at opposite sides of the neck and cap, to leave it exposed for such liquid change; at the same time, the sheet is anchored to the neck, as described, and the bag is comfortably retained in position on the ailing or bruised joint, the legs 12 and 13 being slightly tensioned.

Removal of the wrap is very simple, to allow complete removal of the bag 21, as described, and subsequent replacement. It will be noted that the sheet is insulative, to block heat access from the exterior to the bag, in the case of a cold pack, and to block heat escape to the exterior (i.e. away from the joint), in the case of a hot pack.

The sheet 11 may consist of the commercial product known as STARSKIN, 3 mm #1 smooth skin plush royal 403, produced by St. Albans Rubber Ltd., St. Albans, Herts, England.

I claim:

1. A hot or cold pack retention device, in combination with the pack which is flat and generally circular and having a central neck, comprising
   (a) an elongated, insulative, flexible, relatively thin sheet means having two generally parallel, elongated legs joined to a sheet main portion, each leg substantially longer than its width,
   (b) said main portion forming a hole to fittingly receive said pack neck, the sheet main portion then substantially completely covering, engaging, gripping, and conforming to the shape of the pack, with said legs projecting away from surfaces of the pack at opposite sides of said neck,
   (c) the legs than wrapping about and over the sheet main portion at opposite sides of said neck to hold the pack to a user's body,
   (d) said sheet comprising elastomer foam, and being insulative and bi-directionally stretchable,
   (e) the sheet including a layer of stretchable pile fabric covering the outerside of said elastomer foam, and there being hook elements carried by said legs to removably attach to said fabric layer.

2. The device of claim 1 wherein each leg has width about one-half the overall width of the sheet.

3. The device of claim 1 wherein said sheet comprises NEOPRENE foam.

4. The device of claim 1 wherein sheet is in at least partly stretched condition when wrapped as in (c) of claim 1.

* * * * *